(12) United States Patent
Taneja

(10) Patent No.: US 9,283,197 B1
(45) Date of Patent: Mar. 15, 2016

(54) MORE POTENT AND LESS TOXIC FORMULATIONS OF EPINEPHRINE AND METHODS OF MEDICAL USE

(71) Applicant: Jugal K. Taneja, Tampa, FL (US)

(72) Inventor: Jugal K. Taneja, Tampa, FL (US)

(*) Notice: Subject to any disclaimer, the term of this patent is extended or adjusted under 35 U.S.C. 154(b) by 0 days.

(21) Appl. No.: 14/460,845

(22) Filed: Aug. 15, 2014

(51) Int. Cl.
*A61K 31/137* (2006.01)

(52) U.S. Cl.
CPC .................................. *A61K 31/137* (2013.01)

(58) Field of Classification Search
CPC .................................................... A61K 31/137
See application file for complete search history.

(56) References Cited

FOREIGN PATENT DOCUMENTS

CA    2002643 A   *   5/1990

OTHER PUBLICATIONS

Gherezghiher et al., "Ocular Effects of Adrenergic Stereoisomers in the Rabbit," Journal of Ocular Pharmacology, 1985, vol. 1, No. 1; pp. 19-28.*
MSDS for Hydrochloric Acid Solution, 1.0 M; Scholar Chemistry; Jan. 23, 2009.*
MSDS for Hydrochloric Acid 12N; Scholar Chemistry; Feb. 2, 2009.*

* cited by examiner

*Primary Examiner* — Sreeni Padmanabhan
*Assistant Examiner* — Jody Karol

(57) ABSTRACT

The present invention provides pharmaceutical formulations of levorotatory-epinephrine, l-epinephrine, more potent and less toxic than existing pharmaceutical formulations of epinephrine, along with methods of producing and using these pharmaceutical formulations of l-epinephrine.

7 Claims, No Drawings

MORE POTENT AND LESS TOXIC FORMULATIONS OF EPINEPHRINE AND METHODS OF MEDICAL USE

FIELD OF THE INVENTION

The present invention provides pharmaceutical formulations of levorotatory-epinephrine (l-epinephrine), more potent and less toxic than existing pharmaceutical formulations of epinephrine, along with methods of producing and using these pharmaceutical formulations of l-epinephrine.

BACKGROUND OF THE INVENTION

Epinephrine has a long history of pharmaceutical use that spans many decades since this catecholamine was first chemically synthesized at the turn of the twentieth century. Epinephrine is a sympathomimetic drug that acts on both alpha and beta adrenergic receptors found ubiquitously throughout much of the body. Epinephrine has profound effects on the cardiovascular system. Epinephrine has direct myocardial stimulation that increases the strength of ventricular contraction and cardiac output, positive inotropic action; increases heart rate, positive chronotropic action; and causes vasoconstriction in the veins and many vascular beds, positive vasopressor action. Epinephrine remains the first-line inotrope/vasopressor in many parts of the world and is recognized by the World Health Organization as an essential medicine with many medical uses and forms of administration.

As eye drops, epinephrine provides mydriasis, the dilation of the pupil, during intraocular surgery. As a solution for nebulization, epinephrine provides bronchodilation and relief of bronchospasm to asthmatics and those with chronic obstructive pulmonary disease. As a solution combined with analgesics for injection, including lidocaine for dental applications and bupivacaine for epidural analgesia, epinephrine improves and lengthens pain relief and sensory blockade during surgical procedures. Yet, epinephrine has many life saving uses in emergency room settings. As a solution for intramuscular or subcutaneous injection, epinephrine helps alleviate vasodilation, loss of intravascular fluid volume, hypotension, bronchospasm, and other symptoms associated with anaphylaxis, severe allergic reactions. Injections of epinephrine can also help stop bleeding, such as bleeding associated with peptic ulcers and surgical procedures. As a solution for intravenous injection, epinephrine is used as a critical adjunct in the treatment of cardiac arrest, e.g., to provide return of spontaneous circulation. Lastly, intravenous injection of this vasopressor provides critical care relief of hypotension associated with certain types of shock and fluid refractory shock, including septic shock.

Although epinephrine has many uses, including many life saving uses, existing liquid formulations of epinephrine are associated with reduced potency, less desirable effects, or have the potential to cause harm. Formulations of epinephrine are plagued by two major problems, racemization and oxidation. Racemization is the enantiomeric conversion of l-epinephrine into its less biologically active dextrorotatory isoform, d-epinephrine, which has a significantly low pressor effect; about one-fifteenth that of l-epinephrine. The d-isoform may also affect adrenergic receptor subtypes differently than the l-isoform, resulting in substandard and undesirable effects. Because the United States Pharmacopeia, USP, monograph for epinephrine injection does not include specifications for d-epinephrine content, only total epinephrine content, manufacturers of epinephrine drug products are not required to test the chirality of their formulation and significant racemization occurs, thus leading to a less potent product with less desirable effects. In actuality, the d-epinephrine isoform should be classified as an impurity in an l-epinephrine drug product. It is believed that the epinephrine injection USP monograph does not include specifications for d-epinephrine because preventing its formation through racemization had proven too challenging. Whereas, oxidation of epinephrine can be prevented to a certain extent, including the use of antioxidants. The oxidation of epinephrine's alcohol group forms its less potent ketone form, known as adrenalone, which has little if any beta adrenergic activity. Racemization and oxidation of epinephrine are associated with reduced potency and less desirable effects as the impurities d-epinephrine and adrenalone form at the expense of l-epinephrine.

Drug manufacturers try to deal with the problem of oxidation by adding bisulfite antioxidants and increasing overages, both of which have the potential to cause harm to patients. Preservatives, such as sodium metabisulfite, are added to epinephrine formulations as antioxidants to reduce oxidation and to help keep formulations sterile. Sterilization techniques themselves often result in the loss of total epinephrine, and l-epinephrine, which may be compensated with increased overages. Sodium bisulfite and sodium metabisulfite, bisulfites, can cause mild to severe, life-threatening allergic reactions, including anaphylaxis or asthmatic episodes in susceptible individuals, especially those with sulfite sensitivities. So while epinephrine is indicated for treating anaphylaxis, the presence of sulfites in its formulation puts susceptible patients at great risk of exacerbating their anaphylaxis to the point of death. And for patients who are in other critical situations, such as cardiac arrest or septic shock, such sulfite reactions could greatly worsen the critical condition of these vulnerable patients. Most formulations also use overages of active pharmaceutical ingredient to compensate for degradation of epinephrine content and activity over the course of the product's shelf-life. This results in epinephrine drug products released after manufacturing with a higher than expected activity, which could be hazardous to patients as causing higher infusion and injection doses, thereby increasing side effects such as tachycardia.

In addition to the degradants d-epinephrine and adrenalone, which have been mentioned to have little pharmacological activity compared with l-epinephrine, lesser other degradants include adrenochrome and adrenolotin. A potentially toxic impurity, epinephrine sulfonate, forms by sulfonation reaction in epinephrine drug products containing sulfites.

Due to the deficiencies in existing pharmaceutical formulations of l-epinephrine, the identity, strength, quality, purity, and/or potency of the drug product cannot be adequately assured, or neither can its safety. There exists a great need for a liquid formulation of l-epinephrine that is both preservative-free and sulfite-free, with minimal overage, if any, and with minimal levels of degradants, including d-epinephrine, while maintaining a sterility guarantee. The present invention fulfills this great medical need by teaching improved l-epinephrine formulations, providing new methods of their preparation, and providing methods of safer medicinal use to achieve an improved standard of patient care.

DETAILED DESCRIPTION OF THE INVENTION

Past solutions of epinephrine have included a microbial preservative in order to assure the sterility of the drug product, even if the drug product was a single-use vial used immediately after opening. Sulfites were able to counter the oxidative behavior of epinephrine by reacting with residual oxygen in its container instead of reacting with epinephrine, and thus, sequestered the free oxygen. When dissolution of the epinephrine was carried out by means of addition of diluted hydrochloric acid, HCl, some excess of acid could maintain a low pH near 2.2 and slow the degradation of epinephrine, also by forming inactive sulphonic acid.

Improved methods of preparation of sulfite-free pharmaceutical formulations of epinephrine included the compounding of the drug substance, followed by initial filtration, filling and sterilization. In order to produce and assure a sterile pharmaceutical solution of epinephrine as a drug product for injectable use, and without including preservatives such as metabisulfites, terminal heat sterilization following filling and/or final filtration under aseptic conditions during filling must be employed.

The compounding step utilized an active l-epinephrine pharmaceutical ingredient base, such as l-epinephrine hydrochloride, USP. This compounding step was performed to place the solid/powder active pharmaceutical ingredient into aqueous solution. Water for injection was the solvent. Mixing alone will not bring l-epinephrine into aqueous solution adequately. The pH of the solution must be lowered in order for the l-epinephrine base to dissolve properly. The pH can be lowered with an acid, such as an organic acid, and preferably 1 Normal (1N) hydrochloric acid that serves as a dissolution agent and a pH adjuster. Since the final solution will be injected into patients, the tonicity of the solution must be increased with a tonicity agent. Although various tonicity agents can be employed, the present methods preferably employ the use of sodium chloride as a tonicity agent. The batch formula per mL was 1.1 mg epinephrine base as the drug substance, 8.6 mg sodium chloride as the tonicity agent, 7.26 g hydrochloric acid (1N) as the dissolution agent, additional hydrochloric acid (1N) as a pH adjuster to lower pH to 2.2 to 2.6, and 987.04 mg water for injection as a solvent. Ideally, the compounding step and subsequent filtration step were conducted under inert nitrogen atmosphere to help prevent exposure of epinephrine and its solution to oxygen. It can be seen from this batch formula that a high 10% overage of epinephrine base was used to compensate for degradation over time, when the desired final concentration is 1 mg/mL epinephrine.

The compounded solution of l-epinephrine was then filtered, such as by a 0.22 micrometer filter and transferred to a sterilized, preferably glass, vessel. Filtration of the compounded solution removed any particulates, whether bacterial or undissolved ingredients.

The filtered solution of epinephrine was then filled into sterilized or sterile containers using sterilized filling equipment. Sterile containers included, but were not limited to, glass ampules, glass vials with caps, glass bottles with caps, and syringes to make prefilled syringes or autoinjectors. To help protect the epinephrine solution against oxidation since no metabisulfites were used in the formulation, the filling step was performed under an inert atmosphere of nitrogen that is essentially devoid of oxygen to reduce the residual oxygen content in the empty space of the filled container. This filling step could be performed under aseptic conditions along with additional filtration, such as by a 0.22 micrometer filter integrated with the filling equipment. Alternatively, or additionally, filled containers could be sterilized by heat, such as by using an autoclave or by steam sterilization. Terminal sterilization at a temperature above the boiling point of water, such terminal sterilization at 121° C., with overkill conditions assured sterility guarantee of the final drug product. For example, a $F_0$ of 10 minutes by means of a steered sterilization cycle was initially chosen to reduce the thermal stress on the epinephrine solution. Because thermal stress was not found to degrade epinephrine, over-kill conditions of sterilization could be used. Degradation of epinephrine was found mainly attributed to exposure to oxygen, which was directly related to nitrogen purge accuracy during the production and filling phases, instead of thermal treatment.

The above steps described the overall manufacturing process in making a drug product of preservative-free, sulfite-free solution of epinephrine. Specifically, it was found that this process inclusive of a 10% overage and an in-process pH range of 2.2 to 2.6 produced an epinephrine solution that could support a shelf-life of a 2 mL glass ampule containing 1 mL epinephrine solution for at least 48 months when studied in a climatic chamber at 25° C. for a maximum storage time of 60 months, in a climatic chamber at 30° C. for a maximum storage time of 12 months, and in a climatic chamber at 40° C. for a maximum storage time of 6 months.

However, this drug product produced by this manufacturing process with an in-process pH of approximately 2.5 was found to be inferior, and not only because of its high 10% overage. It was decided to test this epinephrine solution for d-epinephrine content even though there is no such rationale by USP or the industry to do so. When tested for d-epinephrine content by a chiral HPLC analytical method, it was unexpectedly found that approximately 14% of the l-epinephrine had been racemized into d-epinephrine at the product's release. After storage at 25° C. for 6 months, at least 19% of the l-epinephrine was converted to d-epinephrine. The drug product produced in this manner would contain less than 90% l-epinephrine in well under a year, and for all practical purposes, was unsuitable for use.

Producing an epinephrine drug product with a high l-epinephrine content, such as greater than 90%, throughout its shelf-life of over one year seemed impossible in a preservative-free, sulfite-free solution, and had never been accomplished before. Increasing overages above 10% was not a viable solution. Terminal sterilization of the epinephrine solution only contributed to about 4% racemization, so eliminating heat sterilization and depending solely on aseptic filtration would not solve the racemization problem, nor have as strong of a final sterility guarantee in this antimicrobial-free solution. Lowering the in-process pH was not believed possible due to oxidation issues. The lower the pH was to 2.2, the lower the impact was of potential oxygen residues in the solution. The thought of raising the in-process pH above the 2.2-2.6 of previous methods, and allowing for additional oxidation in an antioxidant-free solution, was contradictory to one skilled in the art.

Inadvertently, increasing the in-process pH to 2.8-3.3, unexpectedly reduced the racemization of l-epinephrine to d-epinephrine at release by approximately two-thirds, from 14% to 5%, respectively. To the contrary, these results led to the discovery that in a preservative-free, sulfite-free, l-epinephrine solution, racemization was a more significant problem than expected, even more so than oxidation. This discovery led to new methods of manufacturing sulfite-free, l-epinephrine solution with an in-process pH of 2.8 to 3.3, approximately 3.0, which was a nonobvious solution to the problem of racemization. Most importantly, with these new methods, overages could greatly be reduced.

The new method of preparing a 1 mg/mL solution of l-epinephrine, such as in a glass ampule, has a revised batch formula per mL of: approximately 1.03 mg epinephrine base, as the drug substance, 8.6 mg sodium chloride as the tonicity agent, 7.26 g hydrochloric acid (1N) as the dissolution agent, additional hydrochloric acid (1N) as a pH adjuster to lower pH only to 2.8 to 3.3, and 987.11 mg water for injection as a solvent. The compounding of the drug substance, followed by initial filtration, filling and sterilization are all conducted under inert nitrogen atmosphere to help prevent exposure of epinephrine and its solution to oxygen.

With less than or no more than a 6% overage, and preferably a 3% overage, a viable shelf-life of at least one year, e.g., at least 15 months, was achieved with the new method with more than 90% l-epinephrine content at the end of the shelf-life. A sealed 2 mL glass ampule served as the container for the 1 mL drug product that was tested. However, the drug product solution of the present invention can be made in larger volumes in other sterile containers, including glass vials and bottles, and syringes and autoinjectors; including autoinjectors conducive with the preservative-free formulation. The new and improved formulation with reduced overage also has less than or no more than 6.5% total impurities, including less than or no more than 6% d-epinephrine and less than or no more than 0.5% adrenalone at release; and less than or no more than 12.5% total impurities, including less than or no more than 12% d-epinephrine and less than or no more than 0.5% adrenalone through a shelf-life of at least 12 months, and preferably through a shelf-life of at least 15 months. If aseptic filtration is used without terminal sterilization, these new methods would allow an l-epinephrine drug product to be prepared without any overage of epinephrine base, so that exactly 1.00 mg of epinephrine base is used per mL in the compounding step.

These inventive methods have discovered and achieved new limits for an injectable liquid pharmaceutical formulation of l-epinephrine sterile solution; less than or no more than about 6% d-epinephrine at release, and less than or no more than about 12% d-epinephrine through a shelf-life of at least 12 months; which has never been accomplished before, even if preservatives/sulfites are optionally included in the formulation as alternate embodiments (e.g., preservatives/sulfites up to about 1 mg per mL, such as sodium metabisulfite). Although these injectable liquid pharmaceutical formulations of l-epinephrine sterile solution introduced by this invention can be produced having any desirable concentration of l-epinephrine, they are preferably compounded in an aqueous solution as approximately 1.0 to 1.06 mg/mL l-epinephrine, and further include a tonicity agent, and include no more than about 6% d-epinephrine and no more than about 0.5% adrenalone at release, and no more than about 12% d-epinephrine and no more than about 0.5% adrenalone over a shelf-life of at least 12 months. Such injectable liquid pharmaceutical formulations of l-epinephrine sterile solution taught by this invention have uncompromised potency of l-epinephrine at release and through their shelf-life.

The present invention therefore provides improved methods of formulating safer and more reliable pharmaceutical preparations of epinephrine for medicinal use. Unlike other epinephrine formulations, these improved formulations are preservative-free and sulfite-free so that there are no safety issues for anaphylaxis and no toxic epinephrine sulfonate byproducts. These improved epinephrine formulations have no need for high overages, and use minimal overages, if any to assure reliable dosage. The present methods of this invention preferably use l-epinephrine hydrochloride, USP as the active pharmaceutical ingredient base, although other l-epinephrine active ingredients and salts and combinations thereof can be employed, including epinephrine bitartrate. The present methods of this invention preferably use sterile containers including, but not limited to, glass ampules, glass vials with caps, glass bottles with caps, and syringes to make prefilled syringes or autoinjectors. Other inert gases, instead of or in addition to nitrogen, can be used for the manufacturing process. Other concentrations of sulfite-free, l-epinephrine solution greater or lower than approximately 1 mg/mL can also be prepared using these new methods and in-process pH under nitrogen (inert gas) atmosphere, where nitrogen (inert gas) purge accuracy is inversely related to oxygen exposure during the production and filling phases.

The present invention also includes methods of using these more potent and less toxic liquid formulations of l-epinephrine as eye drops to provide mydriasis during intraocular surgery; as a solution for nebulization to provide bronchodilation and relief of bronchospasm to asthmatics and those with chronic obstructive pulmonary disease; as a solution combined with analgesics for injection, including lidocaine for dental applications and tumescent anesthesia and tumescent liposuction; and bupivacaine for epidural analgesia, to improve and lengthen pain relief and sensory blockade during surgical procedures; as a solution for intramuscular or subcutaneous injection to counter symptoms associated with anaphylaxis or to help stop bleeding associated with peptic ulcers and surgical procedures; as a solution for intravenous injection in the treatment of cardiac arrest, to provide return of spontaneous circulation; and as a solution for intravenous injection to relieve hypotension associated with certain types of shock and fluid refractory shock, including septic shock.

Other variations and embodiments of the invention described herein will now be apparent to those of skill in the art without departing from the disclosure of the invention or the coverage of the claims to follow.

What is claimed is:

1. A liquid pharmaceutical formulation of preservative-free and sulfite-free, 1 mg per mL l-epinephrine sterile solution for uses including injection; said liquid pharmaceutical formulation having a pH between 2.8 and 3.3; said liquid pharmaceutical formulation compounded in an aqueous solution as 1.0 to 1.06 mg/mL l-epinephrine, and further including a tonicity agent; said liquid pharmaceutical formulation having no more than 6.5% total impurities at release, including no more than 6% d-epinephrine and no more than 0.5% adrenalone, and no more than 12.5% total impurities over a shelf-life of at least 12 months, including no more than 12% d-epinephrine and no more than 0.5% adrenalone; said liquid pharmaceutical formulation stored in a container with an inert gas prior to use.

2. The said liquid pharmaceutical formulation of claim 1 compounded in an aqueous solution preferably as 1.03 mg/mL l-epinephrine.

3. The said liquid pharmaceutical formulation of claim 1 further having no more than 12.5% total impurities over a shelf-life of at least 15 months, including no more than 12% d-epinephrine and no more than 0.5% adrenalone.

4. A liquid pharmaceutical formulation of preservative-free and sulfite-free, 1 mg per mL l-epinephrine sterile solution for uses including injection; said liquid pharmaceutical formulation having a pH between 2.8 and 3.3; said liquid pharmaceutical formulation compounded as 1.0 to 1.06 mg/mL l-epinephrine, along with 8.6 mg/mL sodium chloride as the tonicity agent, 7.26 mg/mL of 1 Normal hydrochloric acid as the dissolution agent, 987.11 mg/mL water for injection as a solvent, and with additional hydrochloric acid to adjust pH; said liquid pharmaceutical formulation having less than 6.5% total impurities at release, including less than 6% d-epinephrine and less than 0.5% adrenalone, and less than 12.5% total impurities over a shelf-life of at least 12 months, including less than 12% d-epinephrine and less than 0.5% adrenalone.

5. The said liquid pharmaceutical formulation of claim 4 compounded in an aqueous solution as 1.03 mg/mL l-epinephrine.

6. An injectable liquid pharmaceutical formulation of l-epinephrine sterile solution; said liquid pharmaceutical formulation having a pH between 2.8 and 3.3; said injectable liquid pharmaceutical formulation compounded in an aqueous solution as 1.0 to 1.06 mg/mL l-epinephrine, and further including a tonicity agent; said liquid pharmaceutical formulation including no more than about 6% d-epinephrine and no more than about 0.5% adrenalone at release, and no more than about 12% d-epinephrine and no more than about 0.5% adrenalone over a shelf-life of at least 12 months.

7. The said injectable liquid pharmaceutical formulation of claim 6 further having a concentration of 1 mg per mL l-epinephrine.

\* \* \* \* \*

UNITED STATES PATENT AND TRADEMARK OFFICE
CERTIFICATE OF CORRECTION

PATENT NO. : 9,283,197 B1  
APPLICATION NO. : 14/460845  
DATED : March 15, 2016  
INVENTOR(S) : Taneja Page 1 of 1

It is certified that error appears in the above-identified patent and that said Letters Patent is hereby corrected as shown below:

On the Title Page

Item (72) should read:  
Jugal K. Taneja, Tampa, FL (US);  
Darren Rubin, Largo, FL (US)

Signed and Sealed this  
Tenth Day of September, 2019

Andrei Iancu  
*Director of the United States Patent and Trademark Office*

UNITED STATES PATENT AND TRADEMARK OFFICE
CERTIFICATE OF CORRECTION

PATENT NO. : 9,283,197 B1
APPLICATION NO. : 14/460845
DATED : March 15, 2016
INVENTOR(S) : Taneja Page 1 of 1

It is certified that error appears in the above-identified patent and that said Letters Patent is hereby corrected as shown below:

On the Title Page

Item (71) Applicant and Item (72) Inventor should read:
(71) Applicants and (72) Inventors:
Jugal K. Taneja, Tampa, FL (US);
Darren Rubin, Largo, FL (US)

This certificate supersedes the Certificate of Correction issued September 10, 2019.

Signed and Sealed this
Twenty-second Day of October, 2019

Andrei Iancu
*Director of the United States Patent and Trademark Office*

UNITED STATES PATENT AND TRADEMARK OFFICE
CERTIFICATE OF CORRECTION

PATENT NO. : 9,283,197 B1
APPLICATION NO. : 14/460845
DATED : March 15, 2016
INVENTOR(S) : Jugal K. Taneja et al.

Page 1 of 1

It is certified that error appears in the above-identified patent and that said Letters Patent is hereby corrected as shown below:

On the Title Page

Item (12) should read: -- Taneja et al. --

Item (72) "Jugal K. Taneja, Tampa, FL (US)" should read: -- Jugal K. Taneja, Tampa, FL (US); Darren Rubin, Largo, FL (US) --

This certificate supersedes the Certificate of Correction issued September 10, 2019.

Signed and Sealed this
Tenth Day of December, 2019

Andrei Iancu
*Director of the United States Patent and Trademark Office*

UNITED STATES PATENT AND TRADEMARK OFFICE
CERTIFICATE OF CORRECTION

PATENT NO. : 9,283,197 B1
APPLICATION NO. : 14/460845
DATED : March 15, 2016
INVENTOR(S) : Jugal K. Taneja et al.

It is certified that error appears in the above-identified patent and that said Letters Patent is hereby corrected as shown below:

On the Title Page

Item (12) "Taneja et al." should read:
-- Rubin --

Item (71) "Jugal K. Taneja, Tampa, FL (US); Darren Rubin, Largo, FL (US)" should read:
-- Darren Rubin, Largo, FL (US) --

Item (72) "Jugal K. Taneja, Tampa, FL (US); Darren Rubin, Largo, FL (US)" should read:
-- Darren Rubin, Largo, FL (US) --

Signed and Sealed this
Seventh Day of July, 2020

Andrei Iancu
*Director of the United States Patent and Trademark Office*